(12) United States Patent
Moore

(10) Patent No.: US 7,519,153 B1
(45) Date of Patent: *Apr. 14, 2009

(54) X-RAY METROLOGY WITH DIFFRACTORS

(75) Inventor: Jeffrey A. Moore, San Jose, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 188 days.

This patent is subject to a terminal disclaimer.

(21) Appl. No.: 11/388,298

(22) Filed: Mar. 24, 2006

(51) Int. Cl.
*G01N 23/20* (2006.01)
*G21K 1/06* (2006.01)

(52) U.S. Cl. .............. 378/70; 378/71; 378/85

(58) Field of Classification Search ........... 378/45, 378/49, 50, 70, 85, 88, 71; 250/310, 306, 250/307
See application file for complete search history.

(56) References Cited

U.S. PATENT DOCUMENTS

| | | | | |
|---|---|---|---|---|
| 4,915,463 A | * | 4/1990 | Barbee, Jr. | 359/360 |
| 4,969,175 A | * | 11/1990 | Nelson et al. | 378/146 |
| 5,004,319 A | * | 4/1991 | Smither | 359/570 |
| 5,481,109 A | * | 1/1996 | Ninomiya et al. | 250/310 |
| 6,226,349 B1 | * | 5/2001 | Schuster et al. | 378/84 |
| 6,853,450 B1 | * | 2/2005 | Iwasaki et al. | 356/334 |
| 7,039,158 B1 | * | 5/2006 | Janik et al. | 378/45 |
| 7,076,026 B2 | * | 7/2006 | Verman et al. | 378/85 |
| 7,166,838 B1 | * | 1/2007 | Janik | 250/310 |
| 2004/0131146 A1 | * | 7/2004 | Chen et al. | 378/41 |

* cited by examiner

*Primary Examiner*—Irakli Kiknadze
(74) *Attorney, Agent, or Firm*—Bever, Hoffman & Harms, LLP; Jeanette S. Harms

(57) ABSTRACT

An electron probe microanalysis (EPMA) system includes a graded multilayer diffractor for tightly focusing output x-rays onto an x-ray detector. The graded multilayer construction of the diffractor allows a high x-ray flux to be generated in a small measurement spot, which results in a high measurement throughput. The enhanced measurement efficiency provided by the graded multilayer diffractor can allow an EPMA system to be used as an in-line monitoring tool. The graded multilayer diffractor can include multiple reflecting surfaces. Multiple graded multilayer diffractors can also be used.

15 Claims, 4 Drawing Sheets

X-RAY METROLOGY WITH DIFFRACTORS

BACKGROUND OF THE INVENTION

1. Field of the Invention

The invention is related to the field of metrology, and in particular, to an x-ray analysis system capable of efficient measurements on semiconductor wafers.

2. Related Art

As semiconductor devices continue to shrink to enable greater device density in integrated circuits (ICs), accurately and efficiently measuring the characteristics of the structures that form those devices becomes increasingly difficult. In the realm of thin film composition and thickness measurements, x-ray analysis metrology systems (i.e., metrology systems that measure x-ray emissions from a thin film) are becoming increasingly important for ensuring that semiconductor wafers have been properly processed.

For example, modern gate dielectrics are typically silicon dioxide ($SiO_2$). A small amount of nitrogen is sometimes added to improve the electrical characteristics of the gate dielectric. By directly measuring nitrogen x-ray emissions from a gate dielectric layer, an x-ray analysis metrology system can determine if the oxidation process is providing the proper nitrogen concentration in a thin (e.g., 20 Å or less) gate dielectric.

The two main x-ray analysis metrology techniques are electron probe microanalysis (EPMA) and x-ray fluorescence (XRF). EPMA is a metrology technique in which an electron beam (e-beam) is directed at a thin film to cause the thin film to emit x-rays. Those emitted x-rays can then be analyzed to determine the composition and/or thickness of the thin film. In XRF, an x-ray beam is used instead of an e-beam to generate x-ray emissions from the thin film. Both techniques can provide the type of high-precision compositional analysis capabilities required to evaluate modern semiconductor device structures.

FIG. 1A shows a conventional EPMA system 100 that includes an e-beam source 110, a stage 140 for supporting a test sample 120, a cylindrical crystal (or multilayer) diffractor 130, and an x-ray detector 150. E-beam source 110 directs an e-beam 111 at an analysis spot 125 on test sample 120, thereby causing test sample 120 to emit output x-rays 121.

Note that for clarity, only a portion of output x-rays 121 emitted from test sample 120 are depicted. The actual x-ray emission from test sample 120 in response to e-beam 111 will occur in all directions from analysis spot 125. A portion of those output x-rays 121 are reflected and focused onto x-ray detector 150 by diffractor 130 so that the characteristics (e.g., elemental origin and quantity/ratio) of those output x-rays 121 can be measured. The measurements taken by x-ray detector 150 can then be used to determine the composition and/or thickness of a thin film on test sample 120.

Diffractor 130 and x-ray detector 150 form what is sometimes referred to as a wavelength-dispersive x-ray (WDX) detector. Diffractor 130 is tuned to only reflect a particular x-ray wavelength, which allows x-ray detector to precisely measure the level of a particular element (i.e., the element that generates the x-ray wavelength for which diffractor 130 is tuned) within test sample 120.

High performance XRF systems also sometimes incorporate WDX detectors to provide high-precision measurement capabilities. An XRF system incorporating a WDX detector would operate in substantially the same manner as described above with respect to EPMA system 100, except that e-beam source 110 would be replaced with an x-ray generator for directing a focused x-ray beam (rather than e-beam 111) at analysis spot 125. Collection and measurement of the resulting output x-rays 121 would be performed by diffractor 130 and x-ray detector 150 in the same manner as described above with respect to EPMA system 100.

The speed at which measurements can be taken by EPMA system 100 (or a comparable XRF system) is dependent on the x-ray flux at x-ray detector. Therefore, the larger the amount of x-ray emission that can be reflected and focused by diffractor 130 (onto x-ray detector 150), the more quickly EPMA system 100 can complete a measurement on test sample 120.

Unfortunately, diffractor 130 is not well suited for intercepting a large portion of the total x-ray emission from test sample 120. Diffractor 130 is formed from multiple layers of parallel crystal planes. Incoming x-rays that exhibit incident angles that are very near the Bragg angle are partially diffracted by the multiple crystal planes. X-rays having wavelengths that are integer multiples of the distance between the crystal planes experience constructive interference at diffractor 130, and therefore provide a strong response at x-ray detector 150.

Diffractor 130 can only reflect x-rays that exhibit incident angles with the diffractor that are very near the Bragg angle (the Bragg angle is determined by the x-ray energy and the spacing between crystal planes in the diffractor). Therefore, diffractor 130 can only span a very small arc of the Rowland circle before it can no longer reflect the desired x-ray wavelengths. As a result, the x-ray flux at x-ray detector 150 is relatively low, and metrology operations using EPMA system 100 (and similar XRF systems) can be very time consuming. This throughput problem is exacerbated for thin films that generate relatively low concentrations of the x-ray wavelength of interest (e.g., the low-concentration nitrogen x-rays emitted from a thin gate dielectric layer).

The time consuming nature of conventional x-ray metrology tools has mandated that such tools be used as "off-line" tools in production environments. For example, FIG. 1B shows an exemplary flow diagram for a conventional EPMA tool in a production environment. In a "PERFORM FIRST PROCESS" step 181, a batch (e.g., a cassette) of wafers is processed (e.g., gate oxides are formed on the wafers). A monitor wafer is then selected from the processed batch in a "SELECT MONITOR WAFER" step 182 to begin the metrology operation. An e-beam (111) is then directed at the wafer in a "DIRECT E-BEAM AT MONITOR WAFER" step 183, and the resulting x-rays (121) are focused by a diffractor (130) at an x-ray detector (150) in a "FOCUS X-RAYS W/DIFFRACTOR" step 184. The focused x-rays (131) are then measured by the x-ray detector (150) in a "MEASURE FOCUSED X-RAYS" step 185, and the desired characteristics of the test sample are then determined in a "DETERMINE MONITOR WAFER PROPERTIES" step 186. If additional monitor wafers from the batch of processed wafers are to be evaluated, the process then loops back to step 182. The results of the EPMA measurement(s) on the monitor wafer(s) can then be used to determine if the first process is performing within specification in a "QUALIFY FIRST PROCESS" step 187.

Note that because the EPMA operation(s) of steps 182 through 187 is relatively time consuming (for the reasons described above with respect to FIG. 1A), processing of the batch of wafers from which the monitor wafer(s) being examined in steps 182 through 187 has been selected continues in parallel with that analysis in a "PERFORM SECOND PROCESS" step 190. Therefore, the EPMA analysis performed in steps 182 through 187 is described as an "offline analysis". Unfortunately, offline analysis is generally an undesirable technique, because by the time a problem is discovered by the offline analysis, significant additional (costly) processing may have been performed on the problematic batch of wafers. Furthermore, the additional processing can make subsequent tracing of the root cause of the problem impossible.

Accordingly, it is desirable to provide a system and method for efficiently performing x-ray analysis metrology.

SUMMARY OF THE INVENTION

Conventional wavelength-dispersive x-ray (WDX) detectors for electron probe microanalysis (EPMA) and x-ray fluorescence (XRF) tools incorporate a diffractor for focusing output x-rays onto a x-ray detector. Due to the limited curvature range providing effective Bragg reflection in those diffractors, EPMA and XRF tools are limited to use as offline analysis tools.

By incorporating a graded multilayer diffractor into a WDX detector for an EPMA or XRF system, a significantly larger portion of output x-rays can be focused onto the x-ray detector, thereby allowing the EPMA or XRF measurement, respectively, to be made much more quickly than with conventional tools. This increased measurement speed can allow such EPMA or XRF systems to be integrated into the wafer production process (i.e., the EPMA or XRF tool can be used to perform in-line monitoring of production wafers).

Therefore, an x-ray analysis metrology system for analyzing a test sample can include a probe beam source, a graded multilayer diffractor, and an x-ray detector. The probe beam source can direct a probe beam (e.g. an e-beam or an x-ray beam) onto the test sample. The graded multilayer diffractor can advantageously focus the output x-rays from the test sample. The x-ray detector can capture those focused output x-rays.

In one embodiment, the x-ray analysis metrology system can include a set of graded multilayer diffractors and a set of x-ray detectors, thereby allowing simultaneous measurement of different elements within the test sample. For example, a first graded multilayer diffractor and a first x-ray detector could be configured to measure oxygen x-rays, whereas a second graded multilayer diffractor and a second x-ray detector could be configured to measure nitrogen x-rays. Note that the graded multilayer diffractor can be symmetrical, asymmetrical, cylindrical, spherical, paraboloidal, toroidal, or ellipsoidal in shape.

A method for processing a set of wafers can include performing a first process on the set of wafers to create a processed set of wafers. An inline analysis can then be performed on at least one wafer of the processed set of wafers. This inline analysis can be performed by focusing output x-rays from the wafer onto an x-ray detector using a graded multilayer diffractor. Advantageously, a second manufacturing process can be performed on the processed set of wafers after performing the inline analysis.

In one embodiment, performing the inline analysis can include focusing different sets of output x-rays with different wavelengths using a set of graded multilayer diffractors. In this embodiment, each graded multilayer diffractor can be configured to measure a predetermined element x-ray.

The invention will be more fully understood in view of the following description and drawings.

DETAILED DESCRIPTION OF THE DRAWINGS

Conventional wavelength-dispersive x-ray (WDX) detectors for electron probe microanalysis (EPMA) and x-ray fluorescence (XRF) tools incorporate a cylindrical crystal diffractor for focusing output x-rays onto a x-ray detector. Due to the limited curvature range providing effective Bragg reflection in those crystal diffractors, EPMA and XRF tools are limited to use as offline analysis tools. By incorporating a graded multilayer diffractor into a WDX detector for an EPMA or XRF system, a significantly larger portion of output x-rays can be focused onto the x-ray detector, thereby allowing the EPMA or XRF measurement, respectively, to be made much more quickly than with conventional tools. This increased measurement speed can allow such EPMA or XRF systems to be integrated into the wafer production process (i.e., the EPMA or XRF tool can be used to perform in-line monitoring of production wafers).

Figure 2A:
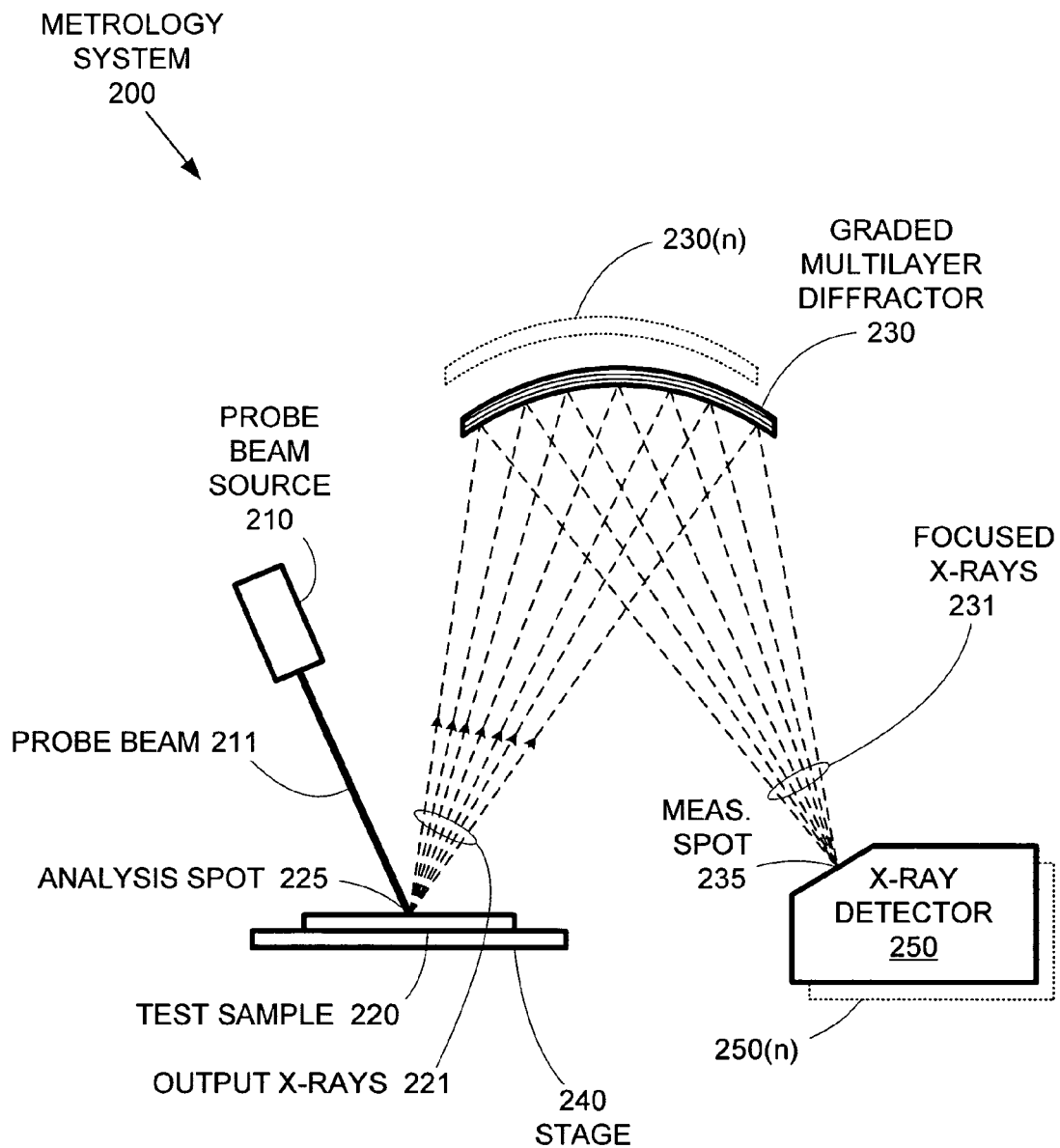
FIG. 2A shows an embodiment of an x-ray analysis metrology system incorporating a graded multilayer diffractor.

FIG. 2A shows an embodiment of an x-ray analysis metrology system 200 that incorporates a graded multilayer diffractor 230 to improve measurement efficiency. Metrology system 200 includes a probe beam source 210, a graded multilayer diffractor 230, a stage 240, and an x-ray detector 250. Stage 240 supports and positions a test sample 220 that includes a thin film or other semiconductor structure to be measured by x-ray analysis metrology system 200.

During a measurement operation, probe beam source 210 directs a probe beam 211 at an analysis spot 225 on test sample 200. In one embodiment, metrology system 200 could be an EPMA system, in which case probe beam 211 would be an e-beam generated by an e-beam source 210. In another embodiment, metrology system 200 could be an XRF system, in which case probe beam 211 would be an x-ray beam generated by x-ray beam source 210.

In either case, probe beam 211 causes test sample 220 to emit output x-rays 221 from analysis spot 225. A portion of those output x-rays 221 are then reflected and focused by graded multilayer diffractor 230 onto x-ray detector 250. Note that while test sample 220 will generally emit output x-rays 221 in all directions from analysis spot 225, only those output x-rays 221 that are intercepted and reflected by graded multilayer diffractor 230 are depicted for clarity.

Figure 1A:
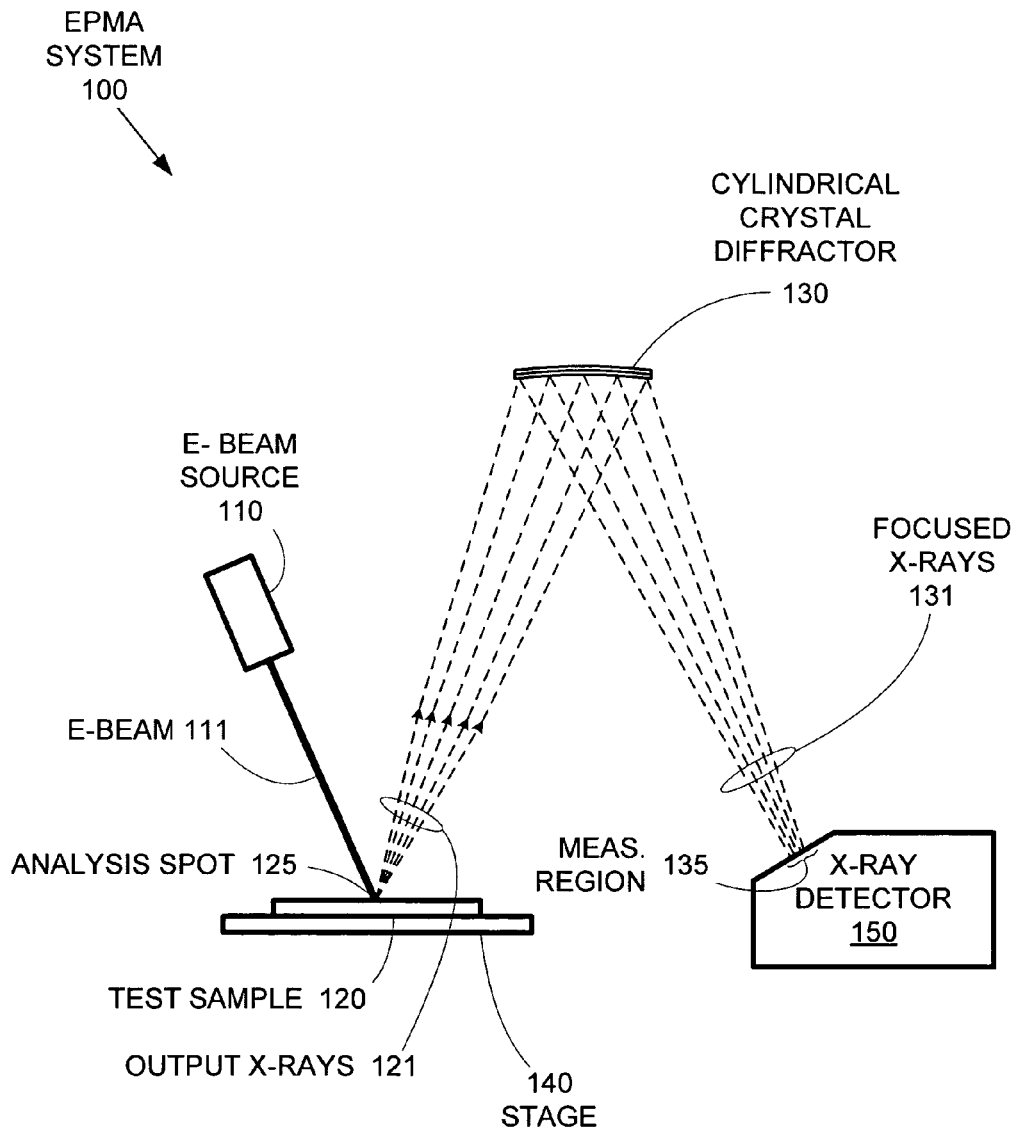
FIG. 1A shows an embodiment of a conventional EPMA system.

Like diffractor 130 shown in FIG. 1A, graded multilayer diffractor 230 is designed to diffract and focus only a small range of x-ray wavelengths. Therefore, graded multilayer diffractor 230 and x-ray detector 250 form a WDX detector that can measure a particular element in test sample 220.

Note that in various embodiments, metrology system 200 can include any number of graded multilayer diffractors 230 (indicated by the dotted outline of graded multilayer diffractor 230($n$)) and any number of corresponding x-ray detectors (indicated by the dotted outline of x-ray detector 250($n$)), thereby allowing metrology system 200 to include multiple WDX detectors for simultaneous measurement of different elements within test sample 220. For example, graded multilayer diffractor 230 and x-ray detector 250 could be configured to measure oxygen x-rays, while graded multilayer diffractor 230($n$) and x-ray detector 250($n$) could be configured to measure nitrogen x-rays (e.g., to allow metrology system to evaluate nitrogen-doped gate oxides).

Unlike cylindrical crystal diffractor 130, which is formed from parallel crystal planes, graded multilayer diffractor 230 includes layers of varying thickness that allow Bragg reflections to be generated across a much larger diffractor area than would be possible with a conventional crystal diffractor. Graded multilayer diffractors, such as the Max-Flux™ optics produced by Osmic Inc., have seen limited use in the realm of optical x-ray metrology (i.e., systems where x-ray reflections from a test sample are measured to determine material characteristics, such as x-ray diffraction (XRD) and x-ray reflectometry (XRR)) for monochromatization of x-rays incident on the test sample. However, in the realm of x-ray analysis metrology systems, graded multilayer diffractors have never been used.

A graded multi-layer diffractor (such as diffractor 230) is formed from a series of alternating layers of high Z (high reflectivity) and low Z (low reflectivity) materials. The materials are selected and sized such that only raw x-rays 221 of a particular wavelength (energy) are reflected. X-rays incident on a surface of one of the high Z layers are partially reflected and partially transmitted. Bragg's law of reflection states an incident set of x-rays is reflected with maximum intensity if the Bragg condition is fulfilled, as indicated by the following:

$$n^*\lambda = 2^*d^*\sin(\theta) \quad \text{[Eqn. 1]}$$

where n is the order of the reflection, $\lambda$ is the wavelength of the incoming x-rays, d is the distance between reflecting surfaces (i.e., the thickness of a high Z/low Z layer pair, sometimes referred to as the period of the multilayer structure), and $\theta$ is the angle of incidence between the incoming x-ray beams and the reflecting surface. When the Bragg condition is satisfied, the distance an x-ray travels before being reflected is a multiple of one half its wavelength, so that reflected x-rays are all in phase, and therefore produce a strong reflected x-ray flux.

Figure 1B:
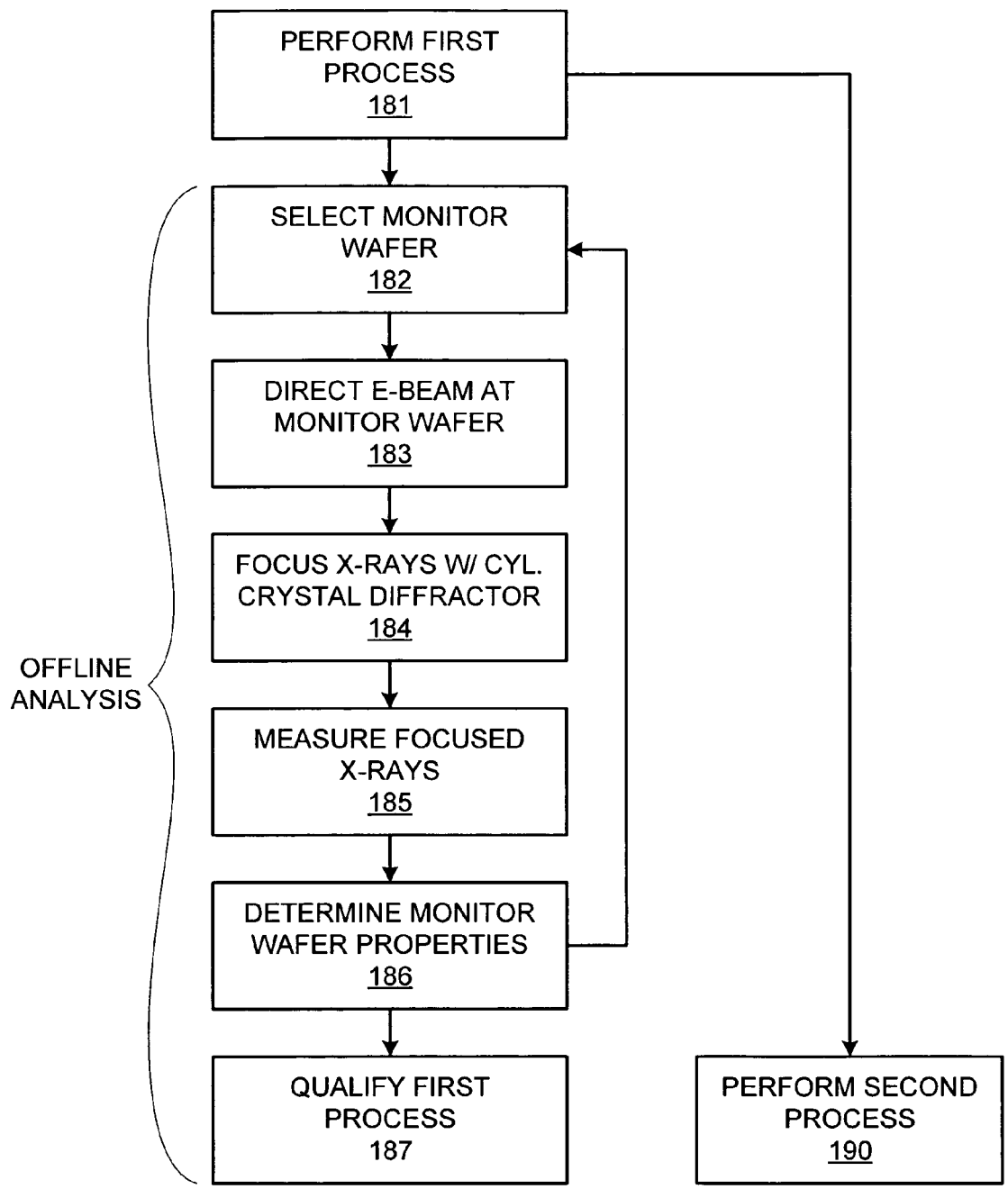
FIG. 1B shows a flow diagram of the use of a conventional EPMA system in a production environment.

As noted above, diffractors (e.g., diffractor 130 in FIG. 1) used in conventional x-ray analysis metrology systems are essentially "parallel layer" structures, in which the parallel crystal layers forming the diffractor act as reflecting surfaces for incoming x-rays. Because those crystalline layers are all parallel, a crystal diffractor is only effective across a relatively small range of incident x-ray angles. Therefore, a crystalline diffractor can only exhibit a small amount of curvature before the Bragg condition is no longer satisfied for incoming x-rays, which results in those x-rays not being reflected. This size limitation is exacerbated by the non-parallel nature of the output x-rays generated from a test sample in response to a probe beam (e.g., output x-rays 121 in FIG. 1A and output x-rays 221 in FIG. 2A all effectively originate and diverge from a point source (i.e., analysis spots 125 and 225, respectively)). Consequently, only a small percentage of raw x-rays 121 can be intercepted by cylindrical crystal diffractor 139, resulting in a relatively low x-ray flux at x-ray detector 150 in conventional EPMA system 100, and hence, a relatively slow measurement speed.

In contrast, the layers in diffractor 230 are "graded", i.e., the thicknesses of the high Z and low Z layers vary across the diffractor to change the distance d between reflecting surfaces across diffractor 230. This layer grading enables efficient reflection of output x-rays 221 that are incident on diffractor 230 across a wide range of incident angles. Therefore, graded multilayer diffractor 230 compensates for the incident angle variation between output x-rays 221 and diffractor 230. The multiple layers making up diffractor 230 are configured such that by properly orienting diffractor 230, x-rays emanating from a particular location (in this case, analysis spot 225 on test sample 220) all satisfy the Bragg condition at diffractor 230. In this manner, the graded multilayer construction of diffractor 230 allows a large portion of output x-rays 221 to be intercepted and focused onto x-ray detector 250, thereby providing a high flux set of focused x-rays 231 that enable high throughput EPMA or XRF metrology.

Note that the actual shape of graded multilayer diffractor 230 can comprise any type of focusing arrangement. In various embodiments, diffractor 230 can comprise a single diffractor surface ("singly curved"), and in various other embodiments, diffractor 230 can comprises multiple diffractor surfaces ("doubly curved"). In various embodiments, graded multilayer diffractor 230 can comprise a symmetrical shape to reduce manufacturing complexity. In various other embodiments, graded multilayer diffractor 230 can comprise an asymmetrical shape to enable alternative positionings relative to test sample 220. In one embodiment, graded multilayer diffractor 230 can comprise a cylindrical or spherical diffractor. However, in another embodiment, graded multilayer diffractor 230 can comprise a paraboloidal, toroidal, or ellipsoidal diffractor to provide improved focusing capabilities.

Typically, an ellipsoidal diffractor will provide the best focusing capabilities. The use of an ellipsoidal diffractor allows either magnification or demagnification to be performed on output x-rays 221, so that measurement spot 255 at x-ray detector 250 can be either larger or smaller than analysis spot 225 on test sample 220. This focusing/defocusing capability can provide flexibility when selecting the sensor system for x-ray detector 250.

In any case, graded multilayer diffractor 230 improves output x-ray collection, thereby significantly improving the throughput capabilities of metrology system 200 over conventional EPMA or XRF tools. As a result, metrology system 200 allows EPMA or XRF to be used as an inline analysis technique (even for difficult gate dielectric nitrogen and oxygen measurements), thereby eliminating the above-described problems associated with offline analysis, while still providing the high precision measurements associated with WDX detectors.

Figure 2B:
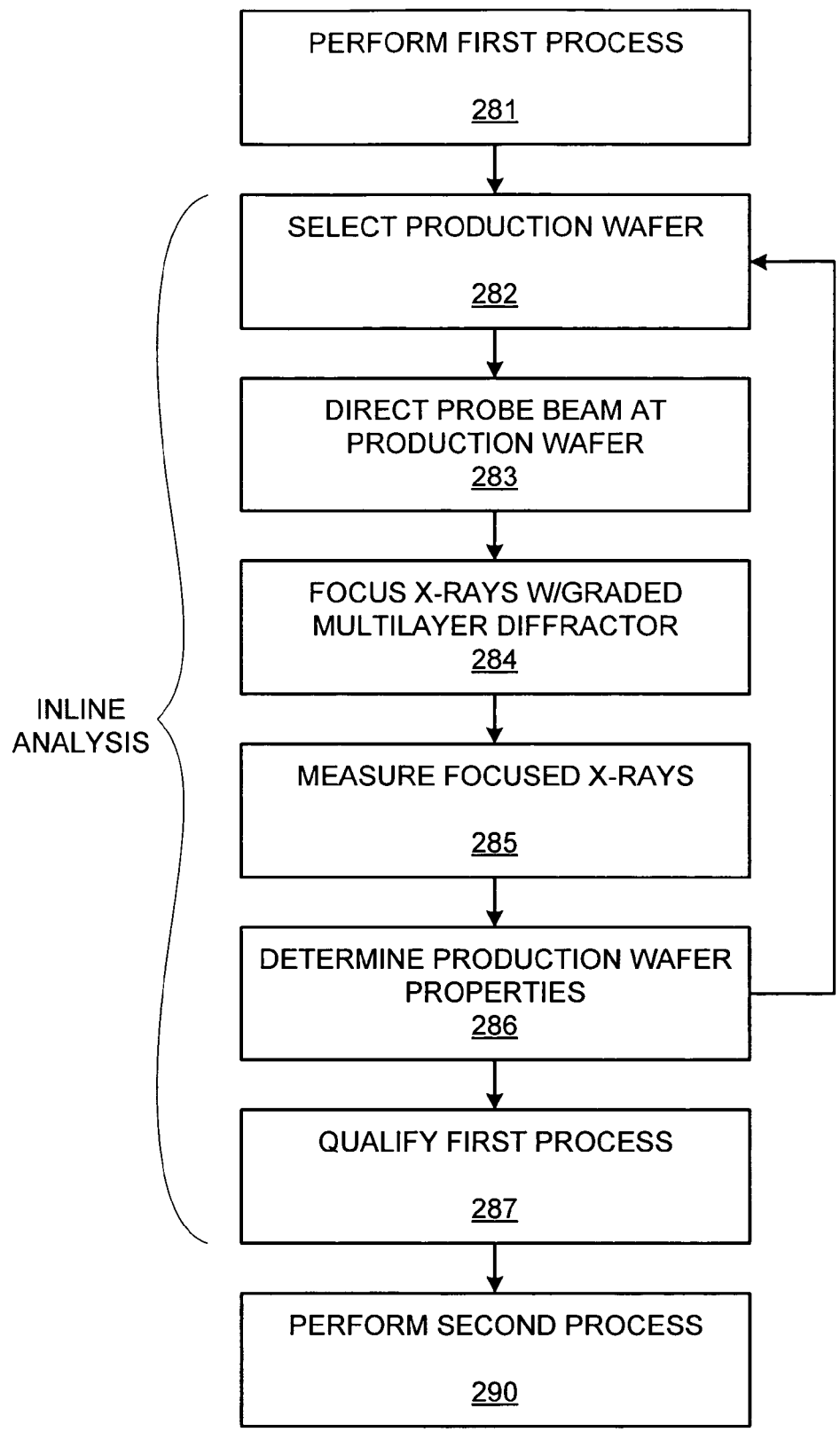
FIG. 2B shows a flow diagram of an inline analysis technique based on x-ray analysis metrology using a graded multilayer diffractor.

FIG. 2B shows a flow diagram of an inline analysis operation that can be performed using metrology system 200 (described above with respect to FIG. 2A). A batch of wafers is processed using a first process in a "PERFORM FIRST PROCESS" step 281. One of the processed wafers is then selected in a "SELECT PRODUCTION WAFER" step 282, and a probe beam (e.g., probe beam 211 in FIG. 2A) is directed at the wafer (e.g., test sample 220 in FIG. 2A) in a "DIRECT PROBE BEAM AT PRODUCTION WAFER" step 282. For EPMA, the probe beam would be an e-beam, and for XRF, the probe beam would be an x-ray beam.

In either case, the resulting output x-rays (e.g., output x-rays 221 in FIG. 2A) emitted by the wafer are reflected onto an x-ray detector (e.g., x-ray detector 250 in FIG. 2A) by a graded multilayer diffractor (e.g., graded multilayer diffractor 230 in FIG. 2A) in a "FOCUS X-RAYS W/GRADED MULTILAYER DIFFRACTOR" step 284. The x-rays are then measured by the x-ray detector in a "MEASURE FOCUSED X-RAYS" step 285 to determine the desired properties of the wafer in a "DETERMINE PRODUCTION WAFER PROPERTIES" step 286. Note that different sets of output x-rays with different wavelengths may be focused and measured by multiple sets of graded multilayer diffractors and x-ray detectors (e.g., graded multilayer diffractor 230($n$) and x-ray detector 250($n$) in FIG. 2A) during steps 284-286.

After step 286, if analysis of multiple wafers is desired, the process can loop back to step 282. Otherwise, the results of the analysis can be used to determine whether the processed wafers meet the specified requirements in a "QUALIFY FIRST PROCESS" step 287. If the results of step 287 are satisfactory, next manufacturing process step can be performed in a "PERFORM SECOND PROCESS" step 290.

By performing the EPMA or XRF analysis between the first and second manufacturing process steps (i.e., between steps 281 and 290), the wastage and troubleshooting issues associated with conventional offline techniques can be avoided. Meanwhile, the high measurement speed enabled by the use of graded multilayer diffractor 230 in metrology system 200 minimizes any throughput degradation on the overall manufacturing process. In this manner, the use of graded multilayer diffractor 230 beneficially allows inline analysis to be performed using EPMA and XRF tools.

Although the invention has been described in connection with several embodiments, it is understood that the invention is not limited to the embodiments disclosed, but is capable of various modifications that would be apparent to one of ordinary skill in the art. Thus, the invention is limited only by the following claims and their equivalents.

The invention claimed is:

1. A method for processing a set of wafers comprising:
   performing a first process on the set of wafers to create a processed set of wafers;
   performing an inline analysis on at least one wafer of the processed set of wafers by focusing output x-rays from the wafer onto an x-ray detector using a graded multilayer diffractor; and
   performing a second process on the processed set of wafers after performing the inline analysis.

2. The method of claim 1, further including directing a probe beam at the wafer to generate the output x-rays.

3. The method of claim 2, wherein the probe beam is one of an e-beam and an x-ray beam.

4. The method of claim 1, wherein performing the inline analysis includes focusing different sets of output x-rays with different wavelengths using a set of graded multilayer diffractors.

5. The method of claim 4, wherein each graded multilayer diffractor is configured to measure a predetermined element x-ray.

6. An x-ray analysis metrology system for analyzing a test sample, the x-ray analysis metrology system comprising:
   a probe beam source for directing a probe beam onto the test sample;
   a graded multilayer diffractor for focusing output x-rays from the test sample; and
   an x-ray detector for capturing the focused output x-rays, wherein the graded multilayer diffractor facilitates inline analysis of production wafers.

7. The x-ray analysis metrology system of claim 6, wherein the probe beam source is one of an e-beam source and an x-ray beam source.

8. The x-ray analysis metrology system of claim 6, wherein the graded multilayer diffractor includes a set of graded multilayer diffractors and the x-ray detector includes a set of x-ray detectors, thereby allowing simultaneous measurement of different elements within the test sample.

9. The x-ray analysis metrology system of claim 6, wherein the graded multilayer diffractor is symmetrical in shape.

10. The x-ray analysis metrology system of claim 6, wherein the graded multilayer diffractor is asymmetrical in shape.

11. The x-ray analysis metrology system of claim 6, wherein the graded multilayer diffractor is cylindrical in shape.

12. The x-ray analysis metrology system of claim 6, wherein the graded multilayer diffractor is spherical in shape.

13. The x-ray analysis metrology system of claim 6, wherein the graded multilayer diffractor is paraboloidal in shape.

14. The x-ray analysis metrology system of claim 6, wherein the graded multilayer diffractor is toroidal in shape.

15. The x-ray analysis metrology system of claim 6, wherein the graded multilayer diffractor is ellipsoidal in shape.

* * * * *